United States Patent [19]

Coffin

[11] Patent Number: 5,492,930

[45] Date of Patent: Feb. 20, 1996

[54] METHOD AND FORMULATION FOR TREATING CNS DISORDERS

[75] Inventor: Vicki L. Coffin, Basking Ridge, N.J.

[73] Assignee: Schering Corporation, Kenilworth, N.J.

[21] Appl. No.: 232,560

[22] Filed: Apr. 25, 1994

[51] Int. Cl.$^6$ .................................................. A61K 31/27
[52] U.S. Cl. ................................. 514/478; 514/879
[58] Field of Search ............................. 514/478, 879

[56] References Cited

U.S. PATENT DOCUMENTS

| | | | |
|---|---|---|---|
| 3,812,263 | 5/1974 | Gilbertson | 424/282 |
| 4,868,327 | 9/1989 | Stiefel | 560/164 |
| 4,978,680 | 12/1990 | Sofia | 514/534 |
| 4,982,016 | 1/1991 | Choi | 568/814 |
| 5,055,489 | 12/1991 | Sofia | 514/483 |
| 5,072,056 | 12/1991 | Stiefel | 568/814 |
| 5,082,861 | 1/1992 | Sofia | 514/534 |

FOREIGN PATENT DOCUMENTS 0531105  3/1993  European Pat. Off. ........ A61K 31/27

OTHER PUBLICATIONS

Metabolites of Felbamate Synthesis of 2(4-hydroxyphenyl)-1,3-propanediol dicarbamate, 2-phenyl-2-hydroxy-1,3-propanediol dicarbamate, and 2-phenyl-1,3-propanediol monocarbamate, Tetrahedron Letters, vol. 42, No. 23, Y. M. Choi, et al., Pergamon Journals, Ltd., pp. 6399–6404 (1986).

Drugs of the Future, vol. 11, No. 11, pp. 931–932 (1986).

Comparative Anticonvulsant Activity and Neurotoxicity of Felbamate and Four Prototype Anti-epileptic Drugs in Mice and Rats, E. A. Swinyard et al., Epilepsia, vol. 27, pp. 27–34 Raven Press (1986).

A Neuropharmacological Evaluation of Felbamate as a Novel Anticonvulsant, H. S. White, et al., Epilepsia, vol. 33(3), pp. 564–572 Raven Press (1992).

Evidence for Anticonvulsant and Neuroprotectant Action of Felbamate Mediated by Strychnine–Insensitive Glycine Receptors, R. T. McCabe, et al., The Journal of Pharmacology and Experimetnal Therapeutics, vol. 264, No. 3 pp. 1248–1252 (1993).

Felbamate is a Potent Anti–Hypoxic Agent in the Hippocampal Slice, R. A. Wallis, et al., Neurology 40 (Suppl. 1) pp. 193 No. 2775 (Apr. 1990).

Glycine Prodrug Facilitates Memory Retrieval in Humans, B. L. Schwartz, et al., Neurology 41, (Sep., 1991) pp. 1341–1343.

Excitatory Amino Acids and Memory; Evidence from Research on Alzheimer's Disease and Behavioral Pharmacology, C. Advokat et al., Neuroscience and Behavioral Reviews vol. 16 pp. 13–24 (1992).

Competitive Antagonism of Glycine at the N–Methyl–D–Asparate (NMDA) Receptor, J. E. Huettner. Biochemical Pharmacology, vol. 41, No. 1, pp. 9–16 (1991).

*Primary Examiner*—Kimberly R. Jordan
*Attorney, Agent, or Firm*—Edward H. Mazer

[57] ABSTRACT

A method for treating CNS disorders and/or improving cognitive ability in a mammal utilizing 2-phenyl-1,3-propanediol monocarbamate is disclosed. Also disclosed are formulations and methods for manufacturing this compound.

7 Claims, 4 Drawing Sheets

5,492,930

METHOD AND FORMULATION FOR TREATING CNS DISORDERS

BACKGROUND OF THE INVENTION

This invention is related to a method and compound for treating CNS disorders and/or improving cognitive ability in a mammal.

Considerable attention has been directed at methods for treating CNS diseases including those disorders which are influenced by changes in excitatory amino acid transmission. These diseases include senile dementia of the Alzheimer's type (SDAT), age-associated memory impairment, Parkinson's Disease, Huntington's Chorea, major affective disorders, neurotic and psychotic disorders, stroke, ischemia and other neurodegenerative disorders. Of particular importance is the treatment of age-related memory impairment, including Alzheimer's disease. As the population has aged, compounds and methods of treatment of this cognitive impairment have increased in importance. It has been estimated that the incidence of Alzheimer's disease increases from 1 to 47% over a twenty year period starting at age 65.

Felbamate, 2-phenyl-1,3 propanediol dicarbamate, has been found to be an effective anticonvulsant agent. *Tetrahedron* Vol. 42, No. 23 pp. 6399–6404 (1986) reports that three major metabolites of felbamate have been identified, including 2-phenyl-1,3-propanediol monocarbamate. This publication also discloses a method of preparing this metabolite. However, this reference does not disclose any utility for this metabolite.

European Patent Publication No. 0 531 105 A1 discloses the use of felbamate for treating and controlling the symptoms of, or for the prevention and control of neurodegenerative disorders associated with the loss of cognitive performance resulting from the loss of cholinergic neurons and/or excessive activation of the N-methyl-D-aspartate (NMDA) receptor complex in human or other warm blooded animals. This European publication discloses the utility of this compound for cognitive deficits of the type produced by Alzheimer's or age-related dementia. This European publication also reports that felbamate may be useful in treatment of disorders such as, for example, hypoxia either alone, e.g. by CO poisoning, near drowning; or combined with ischemic blood flow reduction, e.g. cardiac arrest; stroke; anxiety and neurodegenerative diseases, e.g. Guam ALS, Parkinson's disease, Alzheimer's disease, dementia and lathrism. This publication also discloses the use of 2-phenyl-1,3-propanediol for the manufacture of a medicament for treating and controlling the symptoms of, or for the prevention and control of neurodegenerative disorders associated with or resulting from the loss of cholinergic neurons and/or excessive activation of the NMDA receptor complex in human or other warm blooded mammals. This publication does not present any data to support the conclusion that there is an increase or decrease in activation of NMDA receptors in Alzheimer's disease.

*Drugs of the Future*, Vol 11, No. 11, pp. 931–932 (1986) reports that a minor metabolite of felbamate is 2-phenyl-1, 3-propanediol monocarbamate. No utility is suggested for this metabolite.

It has now been found that the compound 2-phenyl-1,3-propanediol monocarbamate functions as a unique cognitive enhancer and may be effective in the treatment of the various CNS disorders previously noted, including Alzheimer's disease. This compound enhances cognitive abilities by reversing deficits resulting from a loss of cholinergic or NMDA receptor function. Its action is uniquely different from felbamate.

Accordingly, it would be desirable to provide a method of treating CNS disorders in mammals, particularly age-associated memory impairment.

It also would be advantageous to provide a compound and pharmaceutical formulation effective in modulating cognition which will cross the blood-brain barrier and enhance cognition function over a wide dosage range.

SUMMARY OF INVENTION

The present invention is directed at a method for treating a CNS disorder in a mammal by treating said mammal with a CNS-effective amount of the compound 2-phenyl-1,3-propanediol monocarbamate.

The present invention also is directed at a method of treating cognitive deficits in age-associated memory impairment, Parkinson's Disease, Huntington's Chorea, SDAT, major affective disorders (i.e.depression), neurotic disorders (i.e. anxiety), and/or psychotic disorders (i.e. schizophrenia) in a mammal comprising administering to a mammal in need of said treatment an effective amount of 2-phenyl-1,3-propanediol monocarbamate.

The present invention is also directed at a method for improving the cognitive ability of a mammal comprising adminstering to said mammal an effective amount of 2-phenyl-1,3-propanediol monocarbamate.

The present invention also is directed at a pharmaceutical composition comprising 2-phenyl-1,3-propanediol monocarbamate in combination with a pharmaceutically acceptable carrier.

The present invention also is directed at the use of 2-phenyl-1,3-propanediol monocarbamate for the preparation of a medicament effective in treating CNS related diseases, including age-associated memory impairment.

The present invention also is directed a method for preparing a pharmaceutical composition comprising admixing 2-phenyl-1,3-propanediol monocarbamate with a pharmaceutically acceptable carrier.

DETAILED DESCRIPTION OF THE INVENTION

Felbamate, 2-phenyl-1,3-propanediol dicarbamate, has the structure

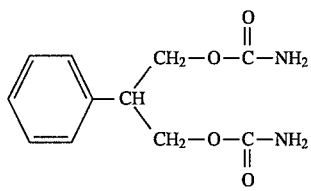

II

This compound is a known anticonvulsant.

A metabolite of felbamate, 2-phenyl-1,3 propanediol monocarbamate, having the structure

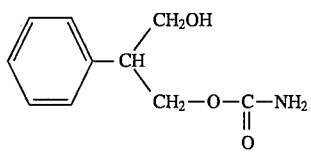

I was believed to be pharmacologically less active than felbamate based upon the test data set forth in Comparative Example I below.

COMPARATIVE EXAMPLE I

Compound I also has been shown to be significantly less effective than felbamate and other known anti-convulsants in blocking electroconvulsive shock (ECS) induced convulsions as shown in Table I following the test procedures described by Swinyard, et al., *Epilepsia*, vol 27, pp 27–34 (1986).

TABLE I

| COMPOUND | $ED_{50}$ (mg/kg-SC) |
|---|---|
| Felbamate | 42.2 |
| 2-phenyl-1,3-propanediol monocarbamate (Compound I) | 173 |
| Dilantin | 5.5 |
| Valproate | 550 |
| Carbamazepine | 12.0 |
| Phenobarbital | 12.0 |

Based on this data, it would not be obvious that compound I, 2-phenyl-1,3-propanediol monocarbamate would be useful in treating CNS-disorders in mammals.

EXAMPLE I

Figure 1:
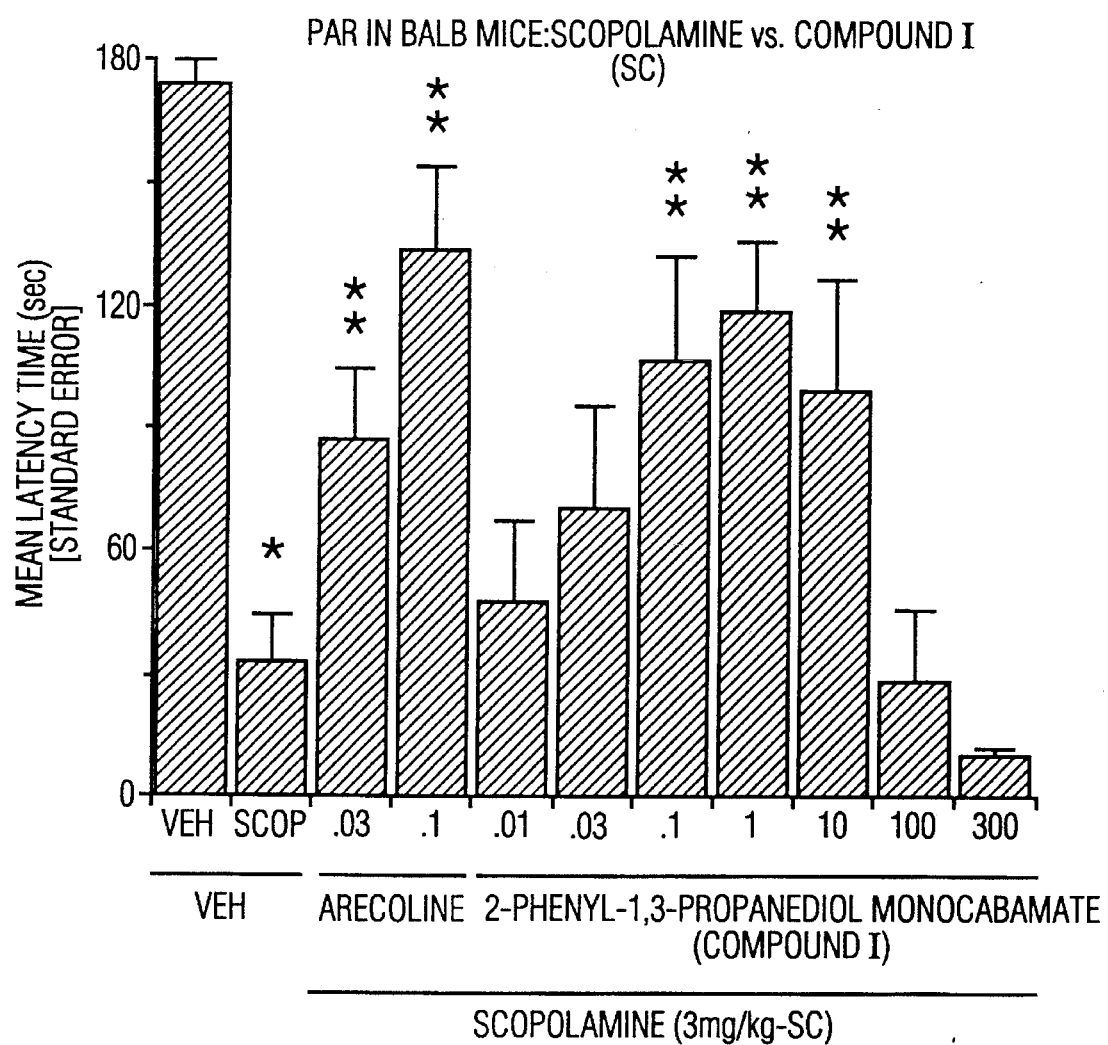
FIGS. 1 and 2 are plots showing the mean latency time in the passive avoidance response (PAR) test of Compound I and arecoline in reversing scopolamine induced cognitive deficits where Compound I is administered subcutaneously (sc) or orally (po).
Figure 2:
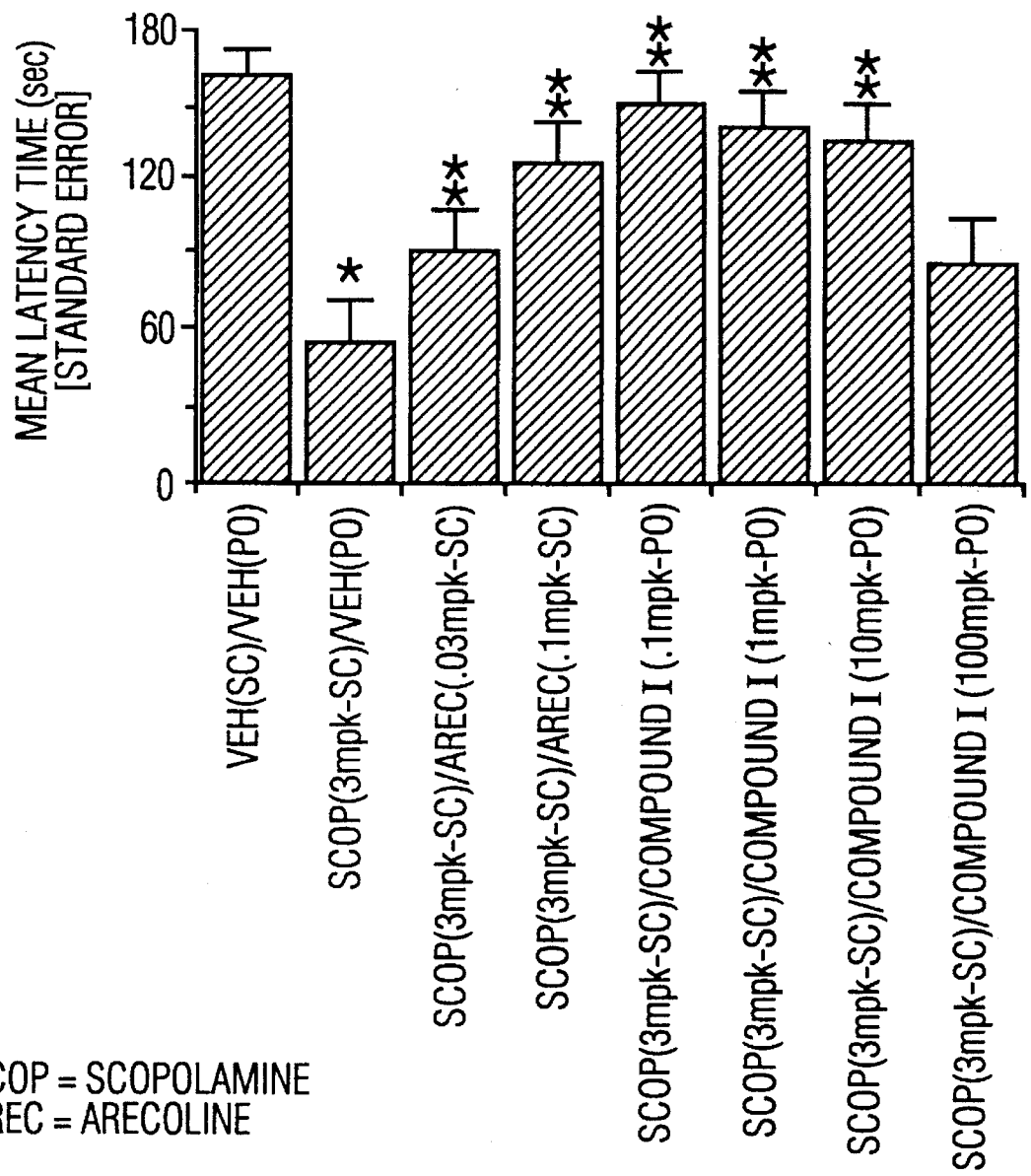
Figure 3:
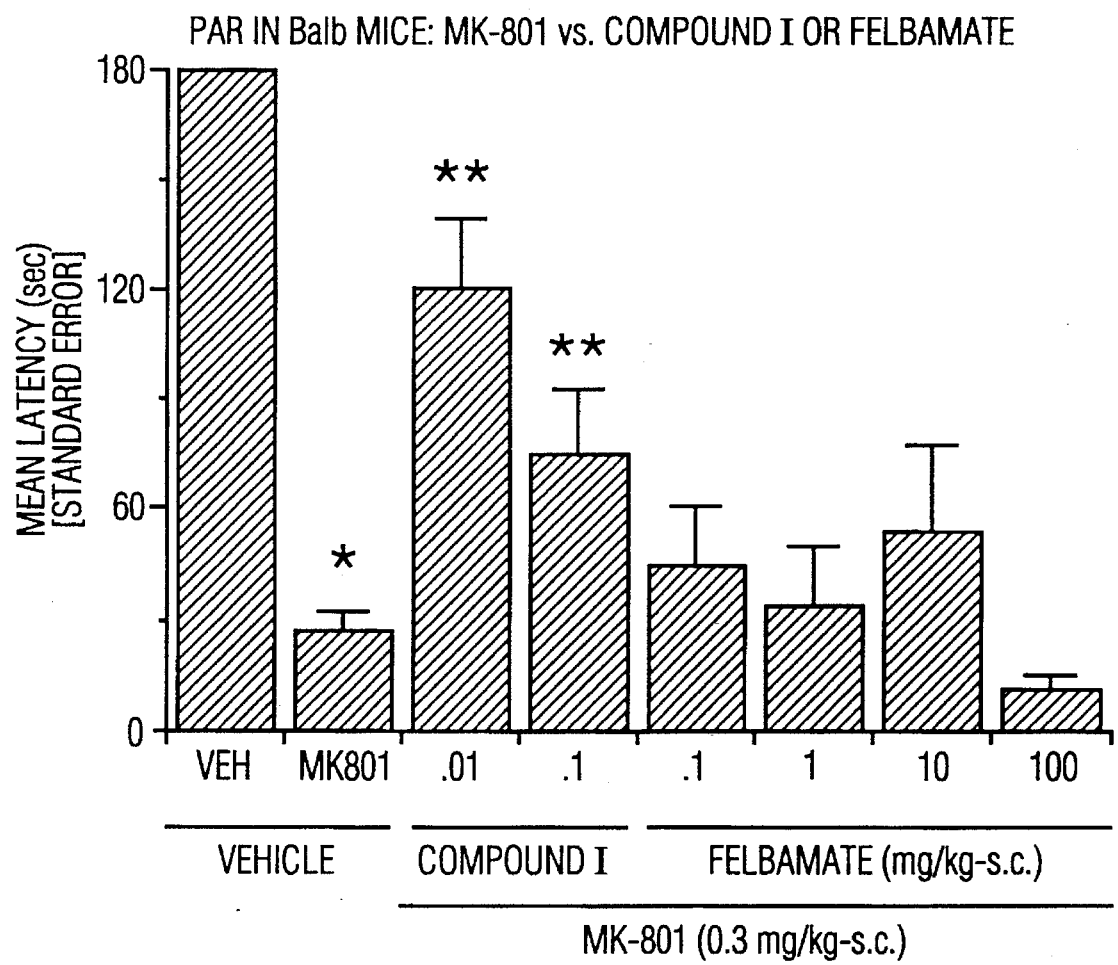
FIG. 3 is a plot showing the mean latency time in the PAR test of felbamate and Compound I in blocking the amnestic effects of MK-801.
Figure 4:
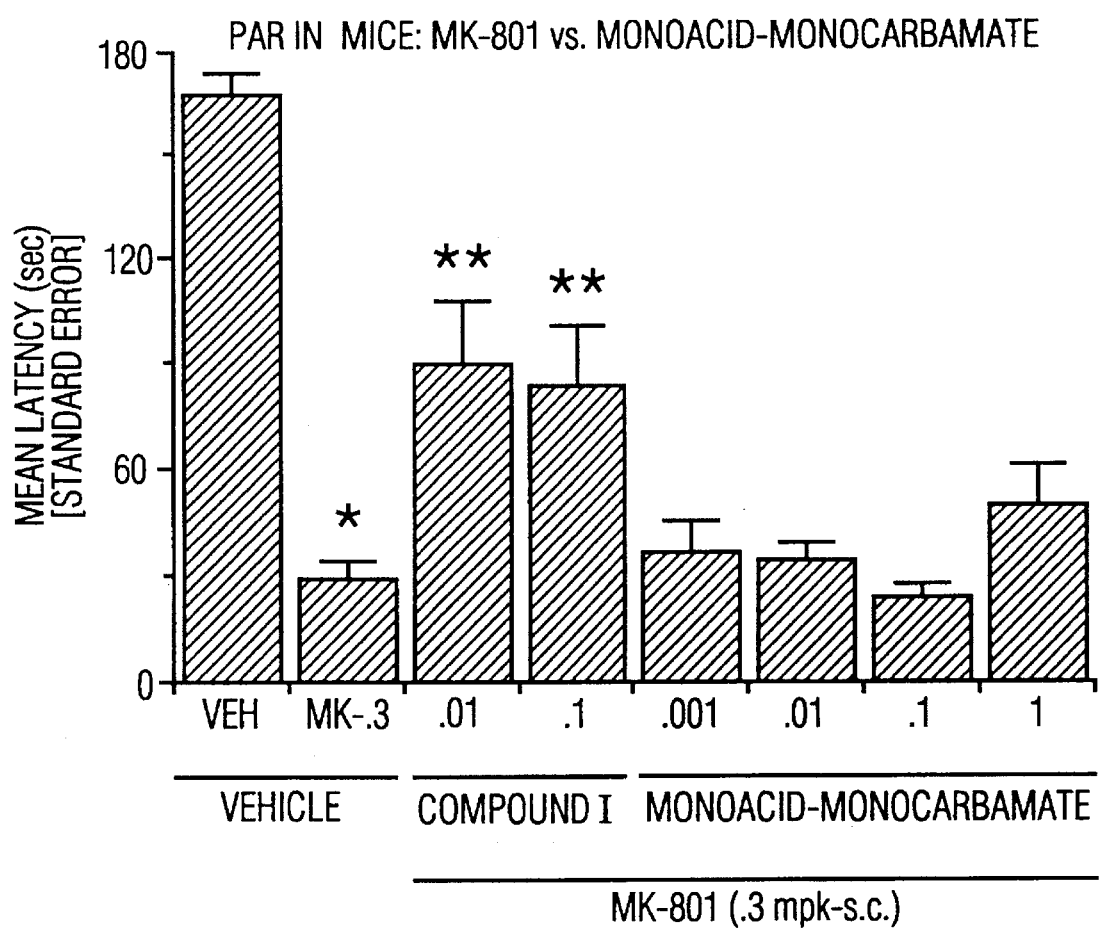
FIG. 4 is a plot showing the mean latency time in the PAR test of Compound I and the corresponding monoacid-monocarbamate.

The surprising utility of Compound I for cognitive enhancement can be demonstrated by reversing a scopolamine induced cognitive deficit. Scopolamine, a muscarinic cholinergic antagonist, is a well-known amnestic for mice in a passive avoidance response test. See, for example Dilts and Berry, *J. Pharmacology and Experimental Therapeutics* 58, 279–285 (1967). As shown by the data presented in FIGS. 1 and 2, surprisingly, it has been found that 2-phenyl-1,3-propanediol monocarbamate is an antagonist for the amnestic effects of scopolamine over a very wide dosage range.

EXAMPLE II

MK-801, a non-competitive antagonist at the NMDA receptor complex, also produces cognitive deficits through a different mechanism than scopolamine (Chiamulera, et al., *Psychopharmacology* Vol. 102, pp551–552 (1990)). The NMDA receptor is strongly implicated in the production of long-term potentiation and subsequent memory processes (Morris, et al., Nature Vol. 319, pp 774–776 (1986)). Blockade of these sites produces amnestic effects in mice on the passive avoidance response. The compound 2-phenyl-1,3-propanediol monocarbamate effectively blocks the amnestic effects of MK-801 in this model at low doses. In contrast, felbamate does not block the effect of MK-801 as shown in FIG. 5. Similarly, in FIG. 6 Compound I is more effective than the corresponding monoacid-monocarbamate, alpha[[(aminocarbonyl)oxy]methyl]benzeneacetic acid, in blocking the effects of MK-801. Based on this data one would not expect felbamate or the corresponding monoacid-monocarbamate to have cognitive enhancing properties.

The data set forth in Examples I and II above suggest that compound I is useful in cognitive enhancement. The data of Examples I and II also show that compound I, 2-phenyl-1, 3-propanediol monocarbamate, is significantly more effective than the corresponding dicarbamate and monoacid-monocarbamate compounds.

2-phenyl-1,3-propanediol monocarbamate has one chiral center. The individual enantiomers as well as the racemic mixture have been found to have the desired activity.

As previously noted, the compound 2-phenyl-1,3-propanediol monocarbamate is known. A preferred method for manufacturing this compound utilizes 2-phenyl-1,3-propanediol as a starting material.

PREPARATIVE EXAMPLE I

Preparation of 2 phenyl-1,3-propanediol (PPD)

U.S. Pat. Nos. 4,982,016; 5,072,056 and 5,091,595 describe methods for preparing PPD from diethylphenylmalonate. U.S. Pat. No. 4,868,327 describes a multistep process for producing PPD from benzaldehyde. U.S. Pat. No. 5,239, 121 discloses a method for making PPD from methyl tropate. A preferred method for making PPD is set forth below:

Preparation of PPD from methyl phenylacetate

Sodium methoxide (24 g, 0.422 moles) is added to 160 mL of toluene under a nitrogen atmosphere, followed by addition of methyl phenylacetate (40 mL, 0.278 moles). The mixture is warmed to 40°–45° C. and methyl formate (27 mL, 0.427 moles) added while maintaining the reaction at 40° to 50° C. Following addition of methyl formate, the reaction mixture is agitated at 40°–50° C. for 30 minutes. A second charge of sodium methoxide (4 g, 0.070 moles) is added to the reaction mixture and the mixture is agitated at 40°–50° C. for 30 minutes. At the end of 30 minutes, analysis of the reaction mixture by HPLC indicates a conversion of methyl phenyl acetate to methyl 2-formyl-2-phenyl acetate sodium salt (greater than 95%, based upon disappearance of methyl phenylacetate starting material), leaving <3% of unreacted methyl phenylacetate. The reaction mixture is cooled to −5° to 0° C. and slowly added to a precooled (−5°–0° C.) mixture of 160 mL water and 40 mL of n-butanol. The reaction vessel is rinsed with 40 mL toluene and added to the quenched mixture. The reaction mixture is maintained at −5° to 2° C. The aqueous phase containing methyl 2-formyl-2-phenylacetate sodium salt is rapidly added to a precooled (−5° to 0° C.) mixture of 120 mL of n-butanol and 32 mL (0.559 mole) of glacial acetic acid. The organic phase containing the protonated enolate is slowly added to a mixture of 200 mL n-butanol and $NaBH_4$ (16 g, 0.422 moles) at −5° to 0° C., while maintaining the temperature of the exothermic reaction at −5° to 5° C. At the end of the addition, the reaction mixture is monitored by HPLC for completion. The reaction mixture is warmed to 10° to 15° C. At the end of 2 hours at 10° to 15° C., 20 mL of methanol is added to the reaction mixture. The reaction mixture is then maintained at 10° to 15° C. until monitoring of the reaction mixture by HPLC indicates a conversion of methyl tropate to 2-phenyl-1,3-propanediol (PPD), leaving <3% unreacted methyl tropate. The reaction mixture is slowly warmed to 25° C., 320 mL water is slowly added, the temperature is maintained at 25° C. and agitated for 5 minutes. The pH is adjusted to about 7.2 with concentrated sulfuric acid (~6.5 mL) and the temperature of the mixture is raised to 40° C. After phase separation, the aqueous layer is extracted again with 80 mL n-butanol (solution yield of PPD is ~90%). The combined butanol extracts are charged with 80 mL water and the pH is adjusted to about 2.2 with concentrated sulfuric acid (~1 mL) to give a mixture of boric acid esters and PPD. After phase separation, the organic layer is washed with 40 mL water. The n-butanol layer is concentrated to give an oil containing a mixture of boric acid esters and PPD. Methanol (160 mL) is charged to the oil, concentrated, and distillation of 160 mL methanol is repeated. Toluene (200 mL) is added and the reaction mixture is azeotropically distilled, under vacuum, to a volume of 160 mL. The concentrated mixture is filtered at about 60° C. then agitated to 25° C. for about 30 minutes. The precipitated PPD is further chilled, filtered, washed at 0° to 5° C. with toluene and dried in a vacuum oven with a nitrogen bleed at 25° C. to give 32.0 grams (81% yield of recovered product, +99.3% purity) of 2-phenyl-1,3-propanediol. Recovery of PPD from the mother liquors increases the yield.

PREPARATIVE EXAMPLE II

Preparation of Monocarbamate from 2-phenyl-1,3-propanediol Method I

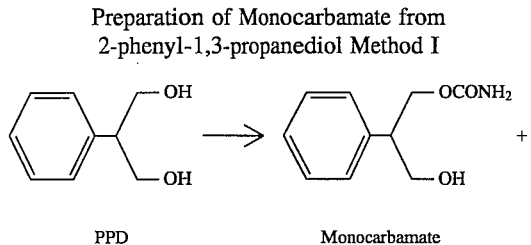

PPD          Monocarbamate

To a three-neck round bottom flask equipped with a thermometer and mechanical stirrer was charged 2-phenyl-1,3-propanediol (PPD) (15.0 g, 98.7 mmol) and 120 mL of 1,2-dichloroethane (EDC). The reaction mixture was heated to 35° to 40° C. and then was charged with a HCl solution in EDC (0.49N, 7.5 mL) A cold HNCO solution in EDC (2.54N, 45.0 mL) was then charged to the reactor mixture slowly in about 30 minutes to produce a 57:43 mixture of monocarbamate and felbamate. The temperature was controlled at 40° to 50° C. The reaction mixture was filtered at 45° to 50° C. to remove felbamate. The wet cake was washed with 20 mL of EDC. The combined filtrates were cooled to 5° to 10° C. for 15 minutes. The precipitate was filtered, washed with EDC and dried in a vacuum oven with a nitrogen bleed to give 5.0 g of crude monocarbamate. The crude monocarbamate could be purified by recrystallization or silica gel column chromatography.

Method II

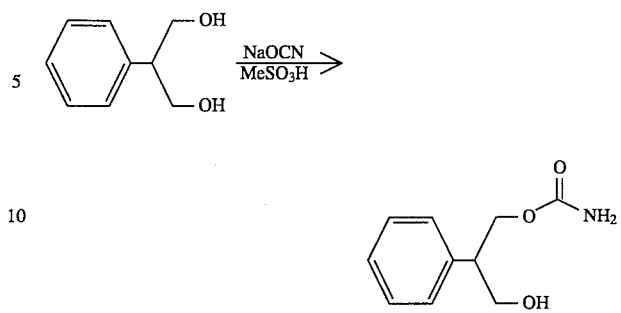

To a 2 L three-neck round bottom flask equipped with a thermometer and mechanical stirrer was charged 2-phenyl-1,3-propanediol (PPD) (200.0 g, 1.32 moles) sodium cyanate (197.0 g, 3.03 moles) and 1 L of acetonitrile. The solution was cooled to 0° C. and methanesulfonic acid (317.4 g, 3.30 moles) was charged slowly in twenty minutes. The temperature is controlled at 0° to 23° C. The solution was then stirred at 15° to 20° C. for another hour. The heterogeneous solution was filtered to afford 1000 mL of filtrate. The filtrate was concentrated to an oil and 200 mL of t-butyl methyl ether was added. Then the organic layer was washed with 200 mL of water. There was some solid fall out in the organic layer. The solid is filtered and the filtrate is concentrated to 63.4 g of solid/oil. This mixture was then recrystallized in t-butyl methyl ether to give 32.9 g of solid which contained approximately 93.3% Monocarbamate, 6.5% Felbamate and 0.2% PPD. This mixture was then combined with 21.08 g of another batch made in a similar way which contained approximately 90.5% monocarbamate, 9.1% felbamate and 0.4% PPD, totaling 53.98 g. The combined mixture was purified by a silica gel column using hexane/isopropanol as an eluent to give 28.32 g of monocarbamate (99% purity).

The dosage of the compound administered will be dependent, in part, on the weight of the mammal, the specific disease and severity of the disease. Typically the daily dosage administered to a mammal may range from approximately 0.001 mg/kg to about 300 mg/kg, preferably about 0.01 mg/kg to 100 mg/kg, most preferably about 1.0 mg/kg to about 30 mg/kg. Preferably the compound is administered orally once per day.

The composition of the present invention may be administered in a variety of forms, including, but not limited to tablets, capsules, and liquids for unit dosage. Preferred dosage forms may include a tablet or capsule in which the active ingredient is intermixed with suitable solid carrier and diluent. Solid carriers and diluents which may be useful in the present invention include, but are not limited to, cellulose derivatives such as cellulose, methyl cellulose, and ethyl cellulose; lactose and sucrose; corn starch, magnesium stearate and stearic acid. Typical formulations and methods of manufacture for both a tablet and a capsule are set forth below:

| TABLET | | |
|---|---|---|
| INGREDIENTS | MG | MG |
| 1. 2-phenyl-1,3-propanediol monocarbamate | 0.07 | 1000 |
| 2. Lactose NF | 137.93 | 100 |
| 3. Corn Starch, Food Grade as a | — | — |

TABLET

| INGREDIENTS | MG | MG |
| --- | --- | --- |
| 10% Paste in Purified Water USP | | |
| 4. Corn Starch, Food Grade | 30 | 62.5 |
| 5. Magnesium Stearate NF | 2 | 12.5 |
| Approximate Tablet Weight | 200 | 1300 |

METHOD OF MANUFACTURE

Mix Item Nos. 1 and 2 in a suitable mixer for 10–15 minutes. Granulate the mixture with Item No. 3. Mill the damp granules through a coarse screen (eg ¼") if necessary. Dry the damp granules. Screen the dried granules if necessary and mix with item No. 4. Mix for 10–15 minutes. Add Item No. 5 and mix for 1–3 minutes. Compress the mixture to appropriate size and weight on suitable tablet press.

CAPSULE

| INGREDIENTS | MG | MG |
| --- | --- | --- |
| 1. 2-phenyl-1,3-propanediol monocarbamate | 0.07 | 500 |
| 2. Lactose NF | 207.93 | 123 |
| 3. Corn Starch, Food Grade | 35 | 70 |
| 4. Magnesium Stearate NF | 7 | 7 |
| Approximate Capsure Weight | 250 | 700 |

METHOD OF MANUFACTURE

Mix Item Nos. 1, 2 and 3 in a suitable blender for 10–15 minutes. Add Item No. 4 and mix for 1–3 minutes. Fill the mixture into suitable two-piece hard gelatin capsules on an encapsulating machine.

While the present invention has been described in connection with certain specific embodiments thereof, it will be evident to one of ordinary skill in the art that many alternatives, modification and variations may be made. All such alternatives, modifications and variations are intended to be included within the spirit and scope of the invention.

What is claimed is:

1. A method for treating a CNS disorder selected from the class consisting of SDAT, age-associated memory impairment, major affective disorders, neurotic disorders and psychotic disorders in a mammal in need of said treatment comprising administering to said mammal a CNS effective amount of 2-phenyl-1,3-propanediol monocarbamate.

2. The method of claim 1 wherein the CNS disorder is age-associated memory impairment.

3. The method of claim 2 wherein the daily dosage of 2-phenyl-1,3-propanediol monocarbamate administered to the mammal ranges between about 0.001 mg/kg and about 300 mg/kg.

4. The method of claim 3 wherein the daily dosage of 2-phenyl-1,3-propanediol monocarbamate administered to the mammal ranges between about 0.01 mg/kg/and about 30 mg/kg.

5. The method of claim 4 wherein the 2-phenyl-1,3 propanediol monocarbamate is administered to said mammal orally.

6. A pharmaceutical composition comprising 2-phenyl-1, 3-propanediol monocarbamate in combination with a pharmaceutically acceptable carrier.

7. A method for preparing a pharmaceutical composition comprising admixing 2-phenyl-1,3-propanediol monocarbamate with a pharmaceutically acceptable carrier.

* * * * *